United States Patent [19]

Sergeant

[11] Patent Number: 4,490,146
[45] Date of Patent: Dec. 25, 1984

[54] LAPAROTOMY SPONGES
[75] Inventor: Timothy L. Sergeant, Seneca, S.C.
[73] Assignee: The Kendall Company, Boston, Mass.
[21] Appl. No.: 471,363
[22] Filed: Mar. 1, 1983
[51] Int. Cl.³ ............................................. A61F 13/00
[52] U.S. Cl. ..................................... 604/358; 604/385
[58] Field of Search .............. 604/358, 378, 374, 367, 604/385, 384

[56] References Cited
U.S. PATENT DOCUMENTS 3,133,538  5/1964  Pratt et al. .......................... 604/362
3,301,257  1/1967  Crowe, Jr. et al. ............ 604/362 X
3,339,548  9/1967  Seltzer ............................. 604/385 X
3,395,707  8/1968  Whalen et al. ....................... 604/385
4,068,666  1/1978  Shiff ..................................... 604/362

Primary Examiner—John D. Yasko
Attorney, Agent, or Firm—Edward J. Scahill, Jr.

[57] ABSTRACT

This disclosure relates to woven gauze dressings known as laparotomy sponges or abdominal packs. More particularly it relates to laparotomy sponges produced with a structure that eliminates a considerable portion of the post-weaving sewing operations associated with prior art dressings of this type.

5 Claims, 5 Drawing Figures

LAPAROTOMY SPONGES

BACKGROUND OF THE INVENTION

This invention is concerned with surgical laparotomy sponges commonly referred to as ABD packs, or abdominal packs. ABD packs, of generally rectangular configuration, are often used in surgical procedures involving the opening of the abdominal wall by surgical incision whereby body organs and delicate body membranes and tissues are exposed. These delicate body members when exposed to the air are subject to radically different environmental conditions from those normally encountered in the moist warmth of the body. It is considered good surgical procedure, therefore, to simulate an environment more nearly approaching the natural environment by using ABD packs moistened with warm saline solution. Such moistened packs are inserted into the cavity to protect and isolate those interior body organs and tissues not directly involved from accidental impact and environmental hazards of the immediate operative area. In the operative area itself ABD packs, either dry or only slightly moistened, are used to sponge and soak up any surplus body fluid present. ABD packs have evolved over many years of surgical practice. Presently used ABD packs are an attempt to retain both the advantages of thin, flexible single layers and the absorptive cushioning and insulating properties of thicker padlike structures. As a result, the ABD pack has traditionally been formed of multiple layers of low-count gauzelike material which are unified by a sewing operation along fairly widely separated lines extending longitudinally or transversely, or in the case of packs of appreciable size, in both directions. Unification has generally been accomplished by lines of machine stitching whether the pack is formed of separated layers or, as is more common, by folding a single width of fabric.

Plied structures of this sort, formed from folded and cut layers of gauze, must be sealed at the edges to prevent the release of cut pieces of yarn, which separate readily from the cut edges of open-mesh, low-count gauze. Such pieces of yarn, if released into and left in a body cavity, lead to pain and irritation post-operatively. It is common practice, therefore, to fold in the raw cut edges of a multi-layered gauze pack and to secure all edges by overedge stitching or by the application of a soft, polymeric sealant. Such sewing or sealing is a substantial element of the cost of such packs, making them so expensive that they are normally reclaimed by laundering and resterilizing.

It is also common practice to incorporate into such dressings a tape at one corner, left outside the body cavity during the operation to serve as a count on the sponges used. Additionally, various radiopaque elements may be incorporated into the sponge, to serve as a tell-tale by X-ray in case that post-operative complications raise the question of a sponge having been left in the body. Such conventional additions may be readily incorporated into the sponges of the prevent invention but are not claimed as novel herein.

It is an object of this invention to produce a multi-layered gauze ABD pack by sealing three selected portions of a gauze blank, cutting the blank longitudinally and laterally along a set of sealed areas, everting the pack thus formed, and completing the pack formation by sealing a single edge of the pack.

PRIOR ART

Attempts have been made in the past to effect economies in the production of abdominal packs by interweaving the yarns at one or more edges of the pack into a selvage edge, combined with sealing the other edges by the use of a polymeric sealing composition, as set forth in U.S. Pat. No. 3,756,241. In general, selvage edges or edges sealed by a polymeric sealant become objectionable when such packs are reclaimed and reused. In a selvage edge, the yarn density, or fabric stiffness, is three to four times the yarn density in the body of the pack. With sealed edges, there is customarily a gradual degeneration in the flexibility of the polymer. Either type of edge may become objectionally stiff on repeated use. By the process of this invention, as set forth below, an abdominal pack is provided in which stiff edges are minimized or eliminated, and the edges are atraumatic.

DESCRIPTION OF THE INVENTION

Figures 3, 4:
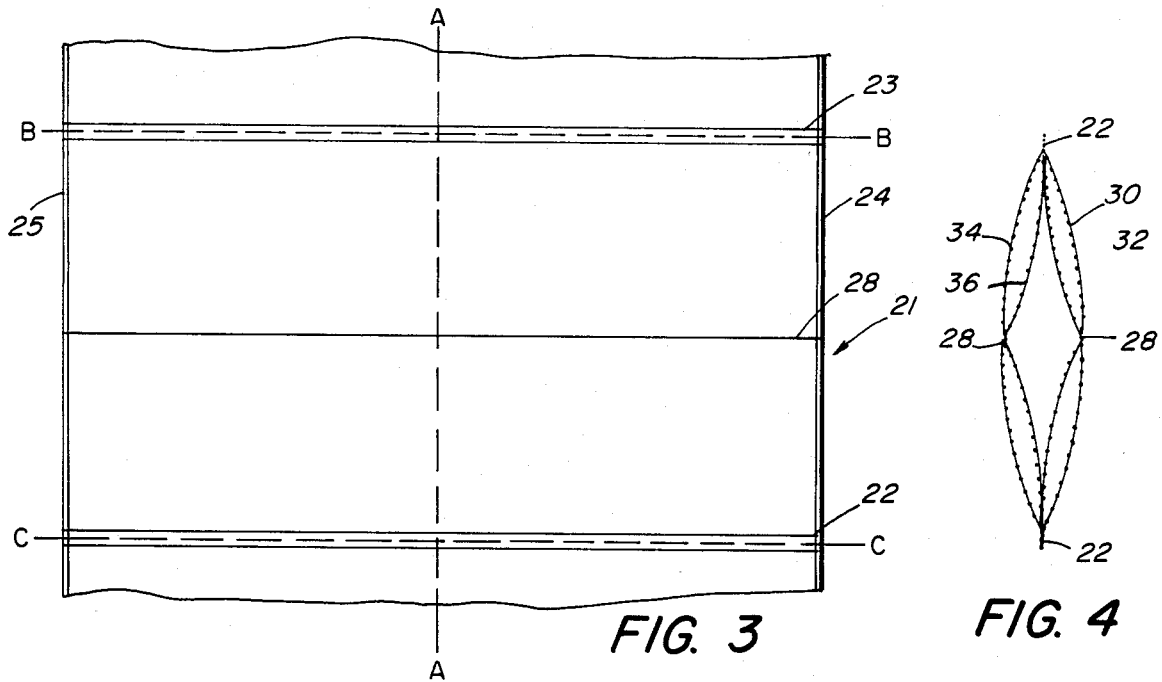
FIG. 3 is a front elevation of a woven gauze blank suitable for use in the practice of this invention.
FIG. 4 is an edge-view of the blank of FIG. 3 as severed along the line A—A.

The process for producing the packs of this invention will be better understood by refering to FIGS. 3 and 4. In FIG. 3 a blank 21 is woven in a gauze construction consisting of a multiplicity of interdependent woven layers interconnected at the warp selvage edges 24, 25 and at the bars 22, 23, which are in the filling or transverse direction. Additionally, in packs of a finished size wherein individual gauze layers are stitched together to stabilize the structure, a yarn or set of yarns 28, running in the filling direction, is common to sets of the gauze plies, securing them together but not securing all plies together. The particular construction of the interior of the blank is seen at FIG. 4, which is a schematic view of the cut edge of the blank of FIG. 3 after it has been cut along the line A—A. Considering the woven blank of FIG. 3 to consist of four layers of gauze, all four layers are secured together at the bars 22, 23.

Paired layers or sets of gauze, 30, 32 and 34, 36 are interwoven in the filling direction by filling yarns 28, 28 which unite the individual plies of gauze in a set, but do not unite the sets. The cut piece, therefore, is evertable and may readily be turned inside out.

The blank 21 of FIG. 3 is shown as woven at a width which is twice the width of the desired finished pack, with the bars 22, 23 serving to unite all the gauze plies at intervals corresponding to the desired length of the pack. Such an arrangement is convenient when abdominal packs of 18 inch square size are to be produced on a 40-inch loom. The fabric is woven in a continuous length, and is subsequently purified, as by boiling and bleaching, to render it white and absorbent in cases where the yarns, or a portion thereof, are of spun cotton.

The various interweaves employed in the practice of this invention are known in the art. Selvage edges need no explanation, and the manner of interweaving various layers of fabric together by filling yarns common to all layers, as in the bars 22, 23 and the filling ties 28 is known practice in, for example, the diaper art. The number of filling ties 28 will vary with the size of the finished pack. For a pack of $12 \times 12$ finished size, one pair of such ties, 46 in FIG. 5, may suffice to stabilize the pack if the ties are located centrally of the blank. For packs 18 inches long two pairs of ties, symmetrically located to give three 6-inch panels, may be preferred.

Figure 1:
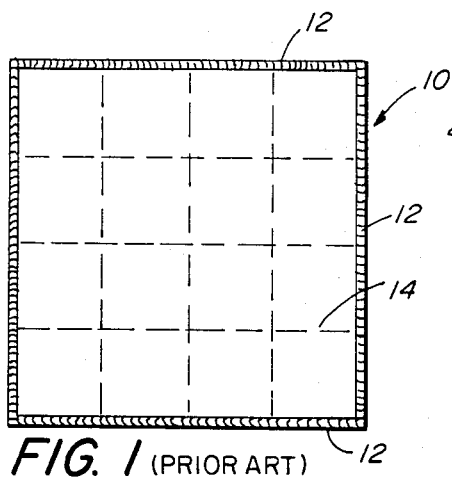
FIG. 1 is a front elevation of a conventional ABD pack, 10, with four externally sealed edges 12 and cross-stitching 14.
Figure 2:
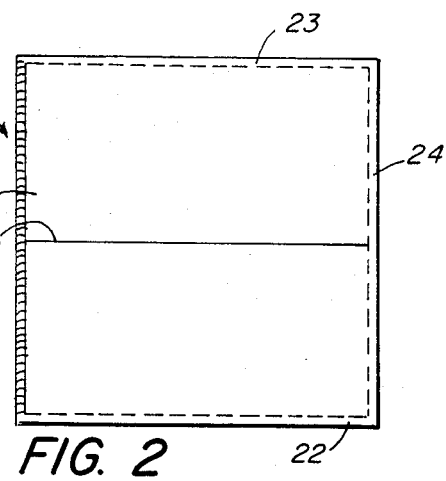
FIG. 2 is a similar elevation of a pack of this invention, 20, with three sealed edges 22, 23, and 24 in the interior of the pack, a single externally sealed edge 26, and lateral tie-in 28 as explained in detail below.

After the fabric has been rendered absorbent, the blank 21 of FIG. 3 is cut along the central line A—A and across the filling bars B—B and C—C. It is then turned inside-out, and the single raw cut edge is secured by overstitching or by the use of a soft, atraumatic polymeric sealant as at 26 in FIG. 2. By this eversion, the relatively firm bar portions 22, 23 and the selvage edge 24 are now disposed on the inside of the pack, as shown by the dotted lines in FIG. 2, thus yielding on three sides of the pack edge portions which are fixed without external sewing or sealant.

Figure 5:
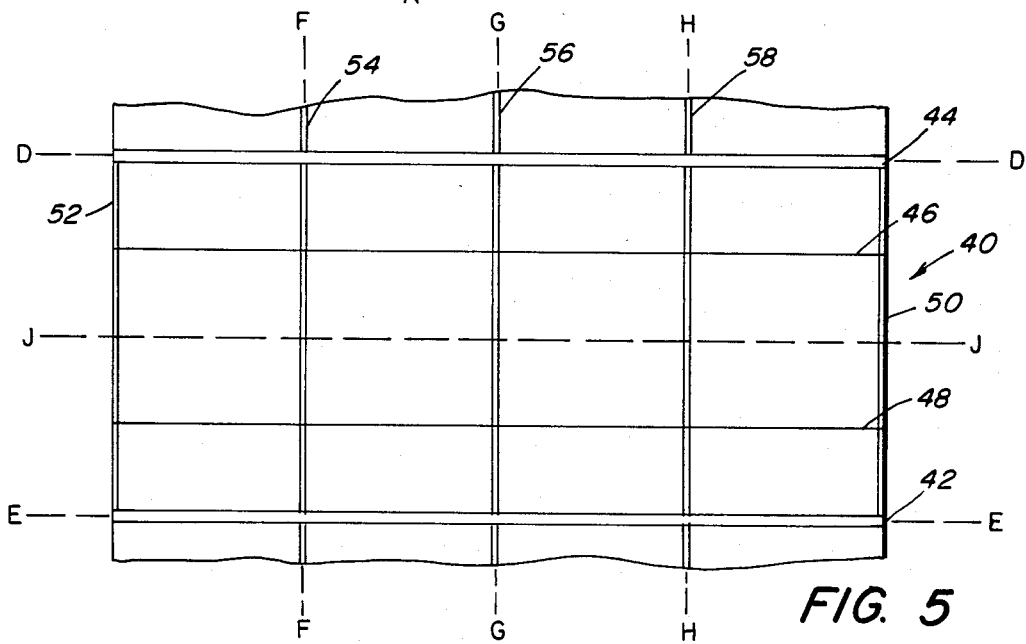
FIG. 5 is a front elevation of another woven gauze blank suitable for use in the practice of this invention.

FIG. 5 represents a gauze blank 40 suitable for use in producing 12-inch square packs on a 50-inch wide loom. As in FIG. 3, a 4-ply gauze fabric is woven with filling bars 42 and 44, filling tie-ins 46 and 48, and selvage edges 50 and 52. Three warpwise sealing bars 54, 56, and 58 seal all four layers of gauze together. As in FIG. 4, the filling tie-ins 46 and 48 unite the two upper gauze layers and the two lower layers, but do not unite all four layers. By severing the blank of FIG. 5 along the lines D,D; E,E; F,F; G,G; H,H; and J,J, eight packs are formed, each sealed externally on three edges and open along the edge created by the cut J,J.

By sealing in this invention is meant uniting the three edges of the cut pack, 22-23-24 or 22-23-25 in FIG. 3, by means of interweaving the yarns in all four layers, or by applying a polymeric sealant. Various polymers are available to form such a sealant, such as a plasticized copolymer of vinyl chloride (50-86%) and vinyl acetate (50%-14%) applied as a heat-sealed tape or by the application of a solvent solution. If desired, such a polymer may be compounded with an equal weight of U.S.P barium sulfate to impart radiopacity to the pack.

In general, it is convenient to form the outside edges of the blank, at 50, 52 in FIG. 5, as interwoven selvage edges and the filling bars 42, 44 also as an interweave.

The warp bars 54, 56, and 58 may also be formed by interweaving selected warp yarns in all four layers, in which case it is convenient to set up the warp yarns constituting the interweave on a separate beam, to compensate for the possibility of excessive contraction due to increased interlacing.

However, if desired, packs may be formed by plying together four layers of gauze and forming all three sealed edges by means of a polymeric sealant, without departing from the spirit of the invention.

SPECIFIC EMBODIMENT OF THE INVENTION

A gauze blank as illustrated in FIG. 3 was woven continuously in a 38-inch width using 31's warp yarns and 39's filling yarns, in a 4-ply construction, with 28 warp yarns and 24 filling yarns per inch. The bars 22, 23 were formed by interweaving the warp and filling yarns in all four layers, to form a fabric count of 112 by 96. Bars 22 and 23 were 19 inches apart.

The filling tie-ins, 28-28 of FIG. 4, were a band of five filling yarns, uniting the top two plies of gauze and the bottom two plies but not all four plies, as shown. These tie-ins were located midway between the bars 22 and 23.

After the continuous fabric was bleached and made absorbent, it was automatically cut along the lines A—A, B—B, and C—C, thus forming two packs which were then turned inside-out to dispose the interwoven edges 22, 23, 24 in the interior of one pack and the edges 22, 23, 25 in the interior of the second pack. The cut edge of each pack was tucked in and secured by a sewn hem.

OTHER EMBODIMENTS OF THE INVENTION.

It will be apparent to those skilled in the art that various sizes of packs may be made by the process of this invention, and that the unification of the plies in a multi-ply gauze structure may be effected by interweaving or by a bonding sealant, or by combinations thereof. The primary objective of the process is to provide a pack in which three of the original external edges of the rectangle are relocated, by everting the cut piece, to be disposed in the interior of the finished pack.

ABD packs have been made in counts of from 14 warp yarns—10 filling yarns to 28 warp yarns—24 filling yarns per inch, and in yarn sized of from 20's to 60's, cotton system, with a 30's to 40's range being customary. Since the function of the pack is to absorb a certain amount of warm, sterile saline solution, it is obvious that the absorption of a pack of given size will vary with the thread count and yarn size. If it is desired to use yarns such as 30's cotton but to change the fabric count, it will be apparent that a gauze of $18 \times 14$ count has only about 60% of the weight of a $28 \times 24$ gauze. In such cases, a 3-ply $18 \times 14$ gauze is produced, with the three plies interwoven by filling tie-ins. By folding such a 3-ply fabric, or by superimposing two layers of such fabric, and subsequently sealing the two layers together by means of a plastic sealant along appropriate bars, followed by cutting along the bars as set forth above, a 6-ply evertable pack of $18 \times 14$ count can be produced which is substantially equal in weight and absorbent capacity to a 4-ply $28 \times 24$ pack of similar size.

What is claimed is:

1. An abdominal pack of generally rectangular configuration and with atraumatic ravel-resistant edges which comprises
    a multiplicity of interdependent plies of open-mesh gauzelike absorbent fabric sealed along all four edges,
    individual sets of said plies being united transversely of the width of said pack by at least one transverse yarnI common to a multiplicity of said plies,
    said pack being sealed along its four edges by a sealing process,
    one sealed edge being disposed on the exterior of said pack,
    said other three sealed edges being disposed in the interior of said pack.

2. The abdominal pack according to claim 1 wherein the sealed edge disposed on the exterior of said pack is a sewn edge and the three edges disposed in the interior of said pack are sealed by a polymeric sealant.

3. The abdominal pack according to claim 1 wherein the sealed edge disposed on the exterior of said pack is sealed by a polymeric sealant and the three edges disposed in the interior of the pack are sealed by interweaving the yarns in each ply of fabric.

4. The abdominal pack according to claim 1 in which the sealed edge disposed on the exterior of said pack is a sewn edge and the three edges disposed in the interior of the pack are sealed by interweaving the yarns in each ply of fabric.

5. The abdominal pack according to claim 1 in which the sealed edge disposed on the exterior of said pack and the three edges disposed in the interior of the pack are all sealed by a polymeric sealant.

* * * * *